United States Patent [19]

White, Jr.

[11] 4,209,617
[45] Jun. 24, 1980

[54] 6,7-DIHYDRO-8H-PYRROLO[2,1-C][1,4]THIAZINE-1(8AH),4(3H)-DIONE

[75] Inventor: Ralph L. White, Jr., Norwich, N.Y.

[73] Assignee: Morton-Norwich Products, Inc., Norwich, N.Y.

[21] Appl. No.: 48,889

[22] Filed: Jun. 15, 1979

[51] Int. Cl.² ............................................. C07D 513/04
[52] U.S. Cl. ...................................................... 544/47
[58] Field of Search ............................................. 544/47

[56] References Cited

U.S. PATENT DOCUMENTS 4,033,955  7/1977  Powell .................... 544/47

Primary Examiner—John M. Ford
Attorney, Agent, or Firm—Anthony J. Franze

[57] ABSTRACT

6,7-Dihydro-8H-pyrrolo[2,1-c][1,4]thiazine-1(8aH),4(3H)-dione is useful as an inhibitor of Angiotensin I converting enzyme.

1 Claim, No Drawings

6,7-DIHYDRO-8H-PYRROLO[2,1-C][1,4]THIAZINE-1(8AH),4(3H)-DIONE

This invention is concerned with the compound 6,7-dihydro-8H-pyrrolo [2,1-c] [1,4]thiazine-1(8aH),4(3H)-dione. This compound is a potent inhibitor of the enzyme responsible for converting the decapeptide Angiotensin I to the octapeptide Angiotensin II. Angiotensin II is the powerful pressor agent implicated as the causative agent in some forms of hypertension.

Of late, it has been recognized that a substance capable of interrupting the pathway whereby Angiotensin II is produced, viz.; the conversion hereabove referred to, presents a useful and effective means of combatting hypertension associated with that pressor agent.

It has been discovered that the compound of this invention is possessed of noteworthy activity in inhibiting Angiotensin I converting enzyme. Thus, in in vitro techniques designed to evince such activity, this compound is highly effective. For example, it inhibits the pure converting enzyme isolated from rabbit lung tissue at a level of about $9.7 \times 10^{-6}$ moles per liter. It is, therefore, a notable Angiotensin I converting enzyme inhibitor.

The compound of this invention is not limited to in vitro manifestations of its converting enzyme inhibiting propensity. Upon oral administration, a dose dependent antihypertensive effect in acute aortic coarctation hypertensive rats is elicited. Such oral dosage as, for example, a suspension in 0.5% Methocel solution of 400 mg/kg elicits a 90.3 mmHg drop in blood pressure.

The method currently preferred for the preparation of the compound of this invention consists in the cyclization of 1-(mercaptoacetyl)-proline, a compound disclosed in U.S. Pat. No. 4,105,776. The following description illustrates that method:

A solution of 1-(mercaptoacetyl)proline (18.0 g, 0.095 mole), dimethylformamide (475 ml, reagent grade), triethylamine (13.2 ml, 0.095 mole) and diphenyl phosphoryl azide (20.5 ml, 0.095 mole) was stirred under ambient conditions for 4.0 hours, poured into $H_2O$ (2.0 liters) and stirred. This solution was extracted with chloroform ($2 \times 750$ ml), saturated with NaCl and extracted with ethyl acetate ($2 \times 750$ ml). Each extract was dried over $MgSO_4$, filtered and concentrated by vacuum distillation to a thin oil. The oils were combined, dissolved in ethyl acetate, washed with $H_2O$ ($3 \times 200$ ml) and dried over $MgSO_4$. The filtered solution was concentrated by vacuum distillation to a solid residue. Recrystallization from 2-propanol and air-drying gave 3.4 g (0.020 mole, 21% yield). The analytical sample was prepared by drying at room temperature in vacuo to give m.p. 116–119°.

$Na[\alpha]_D^{20} = -300.4°$, $Hg[\alpha]_D^{20} = -315.2°$ (C=1.0, ethanol).

Anal. Calcd. for $C_7H_9NO_2S$: C, 49.10; H, 5.30; N, 8.18. Found: C, 49.17; H, 5.34; N, 8.06.

What is claimed is:

1. The compound 6,7-dihydro-8-pyrrolo[2,1-c][1,4]thiazine-1(8aH), 4(3H)-dione.

* * * * *